United States Patent [19]
Bohnenpoll et al.

[11] Patent Number: 5,312,997
[45] Date of Patent: May 17, 1994

[54] SURFACE-ACTIVE PEREOXIDES AND THEIR USE

[75] Inventors: Martin Bohnenpoll; Adolf Schmidt, both of Cologne; Heinrich Alberts, Odenthal, all of Fed. Rep. of Germany

[73] Assignee: Bayer Aktiengesellschaft, Leverkusen, Fed. Rep. of Germany

[21] Appl. No.: 57,230

[22] Filed: May 4, 1993

[30] Foreign Application Priority Data

May 11, 1992 [DE] Fed. Rep. of Germany ....... 4215484

[51] Int. Cl.$^5$ ............................................ C07C 409/00
[52] U.S. Cl. ..................... 568/558; 252/351; 252/352; 252/355; 562/869; 568/559; 568/563; 568/566
[58] Field of Search ............... 568/563, 558, 559, 566, 568/553; 252/351, 352, 355; 562/869; 260/192, 193

[56] References Cited

U.S. PATENT DOCUMENTS

| Re. 27,893 | 12/1973 | Ballini et al. | 568/563 |
|---|---|---|---|
| 3,853,957 | 12/1974 | D'Angelo et al. | 568/563 |
| 3,956,398 | 5/1976 | Schappel | 568/563 |
| 4,158,021 | 6/1979 | Roskott et al. | 568/563 |
| 4,452,737 | 6/1984 | Schmidt et al. | 260/192 |
| 4,476,053 | 10/1984 | Schmidt et al. | 260/192 |
| 5,012,010 | 4/1991 | Suyama et al. | 568/563 |

*Primary Examiner*—Werren B. Lone
*Attorney, Agent, or Firm*—Sprung Horn Kramer & Woods

[57] ABSTRACT

The present invention relates to surface-active peroxides which can be employed as emulsifying initiators for the preparation of low-electrolyte polymer dispersions having a low tendency to foam.

5 Claims, No Drawings

SURFACE-ACTIVE PEREOXIDES AND THEIR USE

The present invention relates to surface-active peroxides which can be employed as emulsifying initiators for the preparation of low-electrolyte polymer dispersions having a low tendency to foam.

During emulsion polymerisation, there is the problem that a highly foaming wastewater remains after the polymer formed has precipitated and must be disposed of, at high costs for environmental protection reasons. The aim of the invention was the development of emulsifiers which are incorporated into the resulting product during the polymerisation and therefore can no longer pollute the wastewater.

It is known to employ azo initiators having surface-active functionalities for the preparation of such dispersions in order to solve this problem (compare EP-A 65 661 and EP-A 65 136).

Although these initiators are suitable for the preparation of low-foaming latices, they are poorly accessible on an industrial scale because of their cumbersome synthesis.

Peroxides having surface-active functional groups offer an improvement. Compounds having a suitable structure are known in principle. Japanese Patent JP 61 192 704 describes peroxide initiators having up to 18 C atoms, which can be employed for polymerisation in solution or in bulk. However, the use of these compounds in emulsion polymerisation has not yet been described. Furthermore, compounds which have more C atoms than the compounds described in this patent are preferably employed to achieve a good emulsifier action.

Initiator/emulsifier systems which are easy to synthesise and with which dispersions having a low tendency to foam and a low electrolyte content can be prepared are provided according to the invention. These comprise new surface-active peroxide compounds with incorporated carboxylic acid or sulphonic acid groups and salts thereof, which simultaneously have emulsifying and activating properties. They initially act as emulsifiers and dissociate during polymerisation. The fragments are incorporated into the polymer and protect the latex particles from coagulation.

The invention relates to surface-active peroxide compounds of the general formula (I)

$$X_n-A-\overset{O}{\underset{\|}{C}}-O-O-R^1, \quad (I)$$

wherein $R^1$ denotes alkyl, cycloalkyl and aryl radicals having 4 to 20 carbon atoms, X denotes the the radicals —COOH and —SO$_3$H and alkali metal, alkaline earth metal or ammonium salts thereof, n denotes an integer in the range from 1 to 6; n preferably represents the numbers 1 and 2, and A denotes alkylene, cycloalkylene and arylene radicals having 10 to 40, preferably 10 to 17, carbon atoms.

The radical A preferably represents a radical of the formula (II)

wherein the radicals $R^2$ and $R^3$ represent H, $C_1$–$C_{40}$-alkyl, $C_3$–$C_{40}$-cycloalkyl, aryl, aralkyl or halogen, with the limitation that the sum of the carbon atoms in the two radicals is greater than 16. The radicals furthermore can be a constituent of a $C_5$–$C_{10}$ aliphatic or $C_6$–$C_{14}$ aromatic ring system.

The peroxides according to the invention have emulsifying properties and can be employed as initiators and emulsifiers for preparation of low-foaming latices in the emulsion polymerisation of olefinically unsaturated monomers.

The compounds according to the invention are reaction products of hydroperoxides with cyclic acid anhydrides.

Examples of suitable hydroperoxides are tert-butyl hydroperoxide, tert-amyl hydroperoxide, cumene hydroperoxide and pinane hydroperoxide.

Cyclic acid anhydrides in the context of the invention are cyclic anhydrides of carboxylic or sulphonic acids having up to 40 carbon atoms, preferably 21 to 40 carbon atoms. They can be halogenated or nitrated.

Examples of suitable cyclic acid anhydrides are: n-octadecylsuccinic anhydride, n-octadecenylsuccinic anhydride, isooctadecenylsuccinic anhydride, isooctadecylsuccinic anhydride, 2-octadecenylsuccinic anhydride, n-eicosylsuccinic anhydride, n-docosenylsuccinic anhydride, n-docosylsuccinic anhydride or mixtures thereof.

These substances can be employed either in the pure form or as industrial mixtures. Mixtures which are characterised in that they are liquid at room temperature are preferred.

The compounds according to the invention can be prepared by the following general method:

The hydroperoxide chosen is dissolved in a suitable solvent and reacted with a cyclic acid anhydride.

Suitable solvents for the reaction are water, organic solvents and two-phase systems of water and an organic solvent which cannot be dissolved in water.

Organic solvents which can be used are those which are inert under the reaction conditions, have an adequate dissolving capacity for the starting materials and the resulting product and can be distilled in vacuo at temperatures of not more than 50° C.

Examples which may be mentioned of possible organic solvents are: benzene, toluene, methylene chloride, chloroform, methyl acetate, ethyl acetate, propyl acetate, butyl acetate and acetonitrile.

Preferred solvents are water, methylene chloride, toluene and a two-phase system of water and methylene chloride.

Preparation of the peroxides according to the invention in water is particularly preferred.

The reaction temperature can in principle be varied within a wide range. Thus, for example, temperatures in the range from 0° to 50° C. are possible. However, the reaction is preferably carried out at temperatures in the range from 15° to 25° C.

The reaction time can be varied, and essentially depends on the reaction temperature and the reactivity of the individual compounds, and is usually in the range from 0.5 to 40 hours. The reaction time is preferably in the range from 1 to 30 hours, particularly preferably in the range from 5 to 20 hours.

The amount of acid anhydride metered in, based on the hydroperoxide employed, is 0.9 to 1.1 mol, preferably 0.95 to 1.05 mol.

If desired, the mixture can be worked up by evaporation of the solvent, if appropriate under a high vacuum, at temperatures of up to 50° C. Preferably, however, the compounds are not dried completely but are further used as solutions. The content of the solutions can vary within a very wide range and can be between 1 and 90 %.

The pH of the solutions can be adjusted to a desired value by addition of acids or bases.

The invention also relates to the use of the peroxide compounds of the formula (I), and of compounds in which the radical A represents radicals having 8 to 17 C atoms, in the emulsion polymerisation of one or more olefinically unsaturated monomers for the preparation of low-electrolyte dispersions having a low tendency to foam. These compounds are employed in amounts of 0.05 to 10 % by weight, preferably 0.1 to 6 % by weight, particularly preferably 1 to 3 % by weight, based on the monomers.

The peroxide compounds either can be employed in the polymerisation as ready-made compounds, or can be produced in situ directly before the start of the polymerisation reaction.

The emulsion polymerisation with the aid of the new peroxide emulsifiers can be carried out batchwise, semi-continuously with a monomer feed, semi-continuously with an emulsion feed or continuously by the known techniques of emulsion polymerisation using these emulsifiers by themselves or in combination with anionic or nonionic surfactants.

In all the polymerisation techniques mentioned, seed lattices which are initially introduced into the reaction vessel or are added during the reaction can also be used in order to influence the particle size distribution.

Seed latices which are intially introduced into the reaction vessel can also be swollen with monomers in the presence of the peroxide emulsifiers according to the invention; this is carried out, if appropriate, until thermodynamic equilibrium is reached, which can take hours to several days and takes place at temperatures which are below the decomposition temperature of the peroxide initiator. Thereafter, the polymerisation can be initiated by heating.

If the anionic groups originating from the peroxide initiator are to be concentrated on the surface of the latex particles, the polymerisation is carried out with the aid of the smallest possible amounts of low molecular weight, readily dialysable emulsifiers in the presence of small amounts of the new peroxide emulsifiers, and the metering in of the peroxide emulsifier is increased towards the end of the reaction and the customary emulsifier is reduced at the same time. The new peroxide emulsifiers simultaneously influence the molecular weight of the polymer chains which form and their charging with hydrophilic groups.

The polymerisation is carried out at temperatures between 35° C. and 90° C., preferably at 45° C. to 75° C., according to the dissociation kinetics of the peroxide compounds.

Possible monomers are all the olefinically unsaturated monomers which can be polymerised with peroxides, for example styrene, α-methylstyrene, butadiene, $C_1$-$C_8$-alkyl acrylates, $C_1$-$C_8$-alkyl methacrylates, acrylonitrile, methacrylonitrile, vinyl chloride, vinyl acetate, ethylene, chloroprene and mixtures thereof.

Relatively small amounts of water-soluble compounds, such as methacrylic acid, acrylic acid, maleic acid half-esters, itaconic acid and itaconic acid half-esters, acrylamide, methacrylamide and the like, can additionally be copolymerised. Furthermore, comonomers carrying functional groups, for example OH or epoxide groups, can also be co-used, such as β-hydroxyethyl (meth)acrylate, β-hydroxy-propyl (meth)acrylate, glycidyl (meth)acrylate and N-methylol or N-methylolalkyl ethers of (meth)acrylamide.

Examples

Series polymerisation experiments were carried out in corked glass bottles of 500 ml capacity with an additional crown cork closure (compare Houben-Weyl, Methoden der Oranischen Chemie (Methods of Organic Chemistry), Volume 14/1, (1961), page 147) with exclusion of atomspheric oxygen. The glass bottles, which were inserted into stainless steel baskets to protect them from shattering, rotated at a speed of 25 revolutions per minute. The temperature of the water-bath was kept constant. Before the bottles were removed from the steel baskets, their corks were drilled through with steel cannulas, in order to release any excess pressure.

The emulsifiers were added as a 1% strength aqueous solution.

To measure the foam regression time, a sample of 100 ml latex was shaken vigorously for 30 seconds. The time until the foam disappeared was then measured.

The percentages and parts stated in the examples and comparison experiments relate to the weight, nless noted otherwise.

Reference is made to the technical literature (H.G. Müller, Colloid. Polym Sci 267, 1113–1116 (1989 and the source literature quoted there) with regard to measurement of the latex particle diameters.

Preparation of the emulsifiers

Example 1

0.72 g (0.003 mol) of decylsuccinic anhydride is stirred in 20 ml of methylene chloride and, after addition of 0.57 g (0.003 mol) of cumene hydroperoxide (80 %), the mixture was stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless suspension which remains is made up to 25.8 g with water.

Example 2

0.97 g (0.003 mol) of hexadecylsuccinic anhydride is stirred in 20 ml of methylene chloride and, after addition of 0.57 g (0.003 mol) of cumene hydroperoxide (80 %), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless suspension which remains is made up to 30.8 g with water.

Example 3

0.89 g (0.003 mol) of tetradecylsuccinic anhydride is stirred in 20 ml of methylene chloride and, after addition of 0.57 g (0.003 mol) of cumene hydroperoxide (80 %), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless suspension which remains is made up to 29.2 g with water.

Example 4

1.06 g (0.003 mol) of octadecylsuccinic anhydride are stirred in 20 ml of methylene chloride and, after addition of 0.57 g (0.003 mol) of cumene hydroperoxide (80 %), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless suspension which remains is made up to 32.6 g with water.

Example 5

0.89 g (0.003 mol) of tetradecylsuccinic anhydride is stirred in 20 ml of methylene chloride and, after addition of 0.38 g (0.003 mol) of tert-butyl hydroperoxide (70 % strength in water), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless liquid which remains is made up to 23.2 g with water.

Example 6

0.97 g (0.003 mol) of hexadecylsuccinic anhydride is stirred in 20 ml of methylene chloride and, after addition of 0.38 g (0.003 mol) of tert-butyl hydroperoxide (70 % strength in water), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless liquid which remains is made up to 24.8 g with water.

Example 7

1.06 g (0.003 mol) of octadecylsuccinic anhydride are stirred in 20 ml of methylene chloride and, after addition of 0.38 g (0.003 mol) of tert-butyl hydroperoxide (70 % strength in water), the mixture is stirred at room temperature for 4 hours. A solution of 0.12 g (0.003 mol) of sodium hydroxide in 20 ml of water is then added dropwise and the mixture is stirred overnight at room temperature. The methylene chloride is distilled off by applying a vacuum. The colourless liquid which remains is made up to 26.6 g with water.

Example 8

0.72 g (0.003 mol) of decylsuccinic anhydride is stirred in 20 ml of methylene chloride and, after addition of 0.38 g (0.003 mol) of tert-butyl hydroperoxide (70 % strength in water), the mixture is stirred at room temperature for 4 hours. A solution of 0.12 g (0.003 mol) of sodium hydroxide in 15 ml of water is then added dropwise and the mixture is stirred overnight at room temperature. The methylene chloride is distilled off by applying a vacuum. The colourless liquid which remains is made up to 19.8 g with water.

Example 9

0.92 g (0.005 mol) of 2-sulphobenzoic anhydride is stirred in 20 ml of methylene chloride and, after addition of 0.64 g (0.005 mol) of tert-butyl hydroperoxide (70 % strength in water), the mixture is stirred at room temperature for 4 hours. A solution of 0.2 g (0.005 mol) of sodium hydroxide in 15 ml of water is then added dropwise and the mixture is stirred overnight at room temperature. The methylene chloride is distilled off by applying a vacuum. The colourless liquid remains is made up to 27.4 g with water.

Example 10

0.77 g (0.005 mol) of hexahydrophthalic anhydride is stirred in 20 ml of methylene chloride and, after addition of 0.64 g (0.005 mol) of tert-butyl hydroperoxide (70 % strength in water), the mixture is stirred at room temperature for 4 hours. A solution of 0.2 g (0.005 mol) of sodium hydroxide in 15 ml of water is then added dropwise and the mixture is stirred overnight at room temperature. The methylene chloride is distilled off by applying a vacuum. The colourless liquid which remains is made up to 24.4 g with water.

Example 11

0.77 g (0.005 mol) of hexahydrophthalic anhydride is stirred in 20 ml of methylene chloride and, after addition of 0.95 g (0.005 mol) of cumene hydroperoxide (80 %), the mixture is stirred at room temperature for 4 hours. A solution of 0.2 g (0.005 mol) of sodium hydroxide in 20 ml of water is then added dropwise and the mixture is stirred overnight at room temperature. The methylene chloride is distilled off by applying a vacuum. The colourless liquid which remains is made up to 30.6 g with water.

Example 12

0.5 g (0.005 mol) of succinic anhydride is stirred in 20 ml of methylene chloride and, after addition of 0.64 g (0.005 mol) of tert-butyl hydroperoxide (70 % strength in water), the mixture is stirred at room temperature for 4 hours. A solution of 0.2 g (0.005 mol) of sodium hydroxide in 15 ml of water is then added dropwise and the mixture is stirred overnight at room temperature. The methylene chloride is distilled off by applying a vacuum. The colourless liquid which remains is made up to 19 g with water.

Example 13

0.5 g (0.005 mol) of succinic anhydride is stirred in 20 ml of methylene chloride and, after addition of 0.95 g (0.005 mol) of cumene hydroperoxide (80 %), the mixture is stirred at room temperature for 4 hours. A solution of 0.2 g (0.005 mol) of sodium hydroxide in 15 ml of water is then added dropwise and the mixture is stirred overnight at room temperature. The methylene chloride is distilled off by applying a vacuum. The colourless liquid which remains is made up to 25.2 g with water.

Example 14

0.112 g (0.002 mol) of KOH, dissolved in 20 ml of water, 0.256 g (0.002 mol) of tert-butyl hydroperoxide (70 %) and 0.7 g (0.002 mol) of octadecenylsuccinic anhydride are stirred vigorously at room temperature for 20 hours. A colourless, slightly cloudy liquid is obtained.

Example 15

0.224 g (0.004 mol) of KOH, dissolved in 40 ml of water, 0.76 g (0.004 mol) of cumene hydroperoxide (80%) and 1.4 g (0.004 mol) of octadecenylsuccinic anhydride are stirred vigorously at room temperature for 20 hours. A colourless milky liquid is obtained.

Example 16

0.224 g (0.004 mol) of KOH, dissolved in 40 ml of water, 0.76 g (0.004 mol) of cumene hydroperoxide (80 %) and 1.41 g (0.004 mol) of octadecylsuccinic anhydride are stirred vigorously at room temperature for 40 hours. A colourless, slightly cloudy liquid is obtained.

| Example 17: Polymerisation experiments with styrene | | | | | | |
|---|---|---|---|---|---|---|
| | A | B | C | D | E | F |
| Deionised boiled [g] | 153.35 | 136.69 | 120.040 | 153.65 | 137.30 | 120.96 |
| 0.1 N sodium hydroxide solution [ml] | 1.81 | 3.62 | 5.430 | 1.50 | 3.01 | 4.51 |
| Styrene [g] | 30.00 | 30.00 | 30.000 | 30.00 | 30.00 | 30.00 |
| Example 1 (1%) [g] | 15.00 | 30.00 | 45.000 | | | |
| Example 2 (1%) [g] | | | | 15.00 | 30.00 | 45.00 |
| Polymerisation time [hours] | 15.00 | 15.00 | 15.000 | 15.00 | 15.00 | 15.00 |
| Polymerisation temp. [°C.] | 70.00 | 70.00 | 70.000 | 70.00 | 70.00 | 70.00 |
| Gross [g] | 566.67 | 565.11 | 566.420 | 569.83 | 570.72 | 568.08 |
| Tare [g] | 367.71 | 365.66 | 366.950 | 370.82 | 371.55 | 368.76 |
| Precipitate, dried [g] | 1.30 | 2.30 | 0.005 | 1.30 | 1.30 | 0.58 |
| Solids [%] | 4.54 | 10.87 | 12.980 | 13.37 | 9.78 | 13.20 |
| pH | 7.00 | 7.15 | 7.000 | 8.40 | 8.40 | 8.50 |
| Electrical conductivity [mS] | 0.36 | 0.33 | 0.460 | 0.09 | 0.13 | 0.17 |
| Photometric measurement | | | | | | |
| Wavelength = 500 nm [nm] | 424.00 | 393.00 | 315.000 | 359.00 | | |
| Wavelength = 600 nm [nm] | 384.00 | 362.00 | 301.000 | 336.00 | | |
| Wavelength = 700 nm [nm] | 369.00 | 353.00 | 299.000 | 331.00 | | |

| Example 18: Polymerisation experiments with styrene | | | | | | |
|---|---|---|---|---|---|---|
| | A | B | C | D | E | F |
| Deionised water, boiled [g] | 153.56 | 137.13 | 120.69 | 153.73 | 137.46 | 121.20 |
| 0.1 N sodium hydroxide solution [ml] | 1.59 | 3.19 | 4.78 | 1.42 | 2.85 | 4.27 |
| Styrene [g] | 30.00 | 30.00 | 30.00 | 30.00 | 30.00 | 30.00 |
| Example 3 (1%) [g] | 15.00 | 30.00 | 45.00 | | | |
| Example 4 (1%) [g] | | | | 15.00 | 30.00 | 45.00 |
| Polymerisation time [hours] | 15.00 | 15.00 | 15.00 | 15.00 | 15.00 | 15.00 |
| Polymerisation temp. [°C.] | 70.00 | 70.00 | 70.00 | 70.00 | 70.00 | 70.00 |
| Gross [g] | 568.84 | 567.95 | 570.44 | 564.83 | 567.20 | 572.46 |
| Tare [g] | 369.34 | 368.56 | 371.09 | 365.66 | 367.50 | 373.02 |
| Precipitate, dried [g] | 1.40 | 0.09 | 0.22 | 0.07 | 0.20 | 0.20 |
| Solids [%] | 11.98 | 14.17 | 13.30 | 13.79 | 12.87 | 14.83 |
| pH | 8.10 | 8.10 | 8.10 | 8.50 | 8.60 | 8.40 |
| Electrical conductivity [mS] | 0.13 | 0.18 | 0.23 | 0.07 | 0.09 | 0.16 |
| Photometric measurement | | | | | | |
| Wavelength = 500 nm [nm] | 368.00 | 184.00 | 155.00 | 334.00 | 230.00 | 129.00 |
| Wavelength = 600 nm [nm] | 339.00 | 176.00 | 150.00 | 315.00 | 219.00 | 124.00 |
| Wavelength = 700 nm [nm] | 335.00 | 172.00 | 147.00 | 309.00 | 214.00 | 121.00 |

| Example 19: Polymerisation experiments with styrene | | | | | | |
|---|---|---|---|---|---|---|
| | A | B | C | D | E | F |
| Deionised | 153.32 | 136.64 | 119.96 | 153.44 | 136.88 | 120.32 |

-continued

|  | A | B | C | D | E | F |
|---|---|---|---|---|---|---|
| water. boiled [g] |  |  |  |  |  |  |
| 0.1 N sodium hydroxide solution [ml] | 1.84 | 3.67 | 5.51 | 1.72 | 3.44 | 5.15 |
| Styrene [g] | 30.00 | 30.00 | 30.00 | 30.00 | 30.00 | 30.00 |
| Example 5 (1%) [g] | 15.00 | 30.00 | 45.00 |  |  |  |
| Example 6 (1%)[g] |  |  |  | 15.00 | 30.00 | 45.00 |
| Polymerisation time [hours] | 15.00 | 15.00 | 15.00 | 15.00 | 15.00 | 15.00 |
| Polymerisation temp. [°C.] | 70.00 | 70.00 | 70.00 | 70.00 | 70.00 | 70.00 |
| Gross [g] | 563.56 | 570.72 | 567.00 | 566.81 | 571.05 | 567.85 |
| Tare [g] | 364.19 | 371.20 | 367.20 | 366.44 | 371.39 | 368.28 |
| Precipitate, dried [g] | 0.52 | 0.17 | 0.14 | 4.70 | 1.10 | 0.46 |
| Solids [%] | 14.31 | 14.67 | 14.85 | 9.06 | 13.97 | 14.67 |
| pH | 6.90 | 7.40 | 7.10 | 7.40 | 7.60 | 7.80 |
| Electrical conductivity [mS] | 0.12 | 0.20 | 0.28 | 0.10 | 0.15 | 0.20 |
| Photometric measurment |  |  |  |  |  |  |
| Wavelength = 500 nm [nm] | 218.00 | 134.00 | 130.00 | 534.00 | 347.00 | 187.00 |
| Wavelength = 600 nm [nm] | 130.00 | 123.00 | 475.00 | 327.00 | 170.00 | 206.00 |
| Wavelength = 700 nm [nm] | 127.00 | 119.00 | 439.00 | 313.00 | 163.00 | 201.00 |

| Example 20: Polymerisation experiments with styrene |
|---|

|  | A | B | C | D | E | F |
|---|---|---|---|---|---|---|
| Deionised water. boiled [g] | 153.54 | 137.08 | 120.63 | 153.03 | 136.06 | 119.09 |
| 0.1 N sodium hydroxide solution [ml] | 1.61 | 3.23 | 4.84 | 2.13 | 4.26 | 6.38 |
| Styrene [g] | 30.00 | 30.00 | 30.00 | 30.00 | 30.00 | 30.00 |
| Example 7 (1%) [g] | 15.00 | 30.00 | 45.00 |  |  |  |
| Example 8 (1%) [g] |  |  |  | 15.00 | 30.00 | 45.00 |
| Polymerisation time [hours] | 15.00 | 15.00 | 15.00 | 15.00 | 15.00 | 15.00 |
| Polymerisation temp. [°C.] | 70.00 | 70.00 | 70.00 | 70.00 | 70.00 | 70.00 |
| Gross [g] | 512.10 | 565.75 | 567.27 | 567.26 | 571.62 | 569.10 |
| Tare [g] | 372.32 | 365.70 | 366.98 | 367.71 | 371.57 | 368.77 |
| Precipitate, moist [g] | 0.50 | 0.80 | 0.90 | 0.40 | 5.60 | 1.40 |
| Precipitate, dried [g] | 0.31 | 0.70 | 0.50 | 0.37 | 1.80 | 0.90 |
| Solids [%] | 13.84 | 14.66 | 14.87 | 13.65 | 14.05 | 14.61 |
| Theory [%] | 15.10 | 15.19 | 15.29 | 15.11 | 15.21 | 15.32 |
| pH | 7.50 | 7.60 | 7.40 | 6.60 | 6.30 | 6.60 |
| Electrical conductivity [mS] | 0.12 | 0.19 | 0.27 | 0.21 | 0.39 | 0.55 |
| Photometric measurement |  |  |  |  |  |  |
| Wavelength = 500 nm [nm] | 278.00 | 164.00 | 108.00 | 244.00 | 188.00 | 157.00 |
| Wavelength = 600 nm [nm] | 268.00 | 159.00 | 102.00 | 224.00 | 178.00 | 151.00 |
| Wavelength = 700 nm [nm] | 262.00 | 158.00 | 96.00 | 214.00 | 172.00 | 147.00 |

| Example 21: Polymerisation experiments with styrene |
|---|

|  | A | B | C | D | E | F |
|---|---|---|---|---|---|---|
| Deionised water. boiled [g] | 152.63 | 135.26 | 117.89 | 152.28 | 134.56 | 117.89 |
| 0.1 N sodium hydroxide solution [ml] | 2.53 | 5.06 | 7.59 | 2.88 | 5.76 | 8.65 |
| Styrene [g] | 30.00 | 30.00 | 30.00 | 30.00 | 30.00 | 30.00 |
| Exampple 9 (1%) [g] | 15.00 | 30.00 | 45.00 |  |  |  |
| Example 10 (1%)[g] |  |  |  | 15.00 | 30.00 | 45.00 |
| Polymerisation | 15.00 | 15.00 | 15.00 | 15.00 | 15.00 | 15.00 |

-continued

| | | | | | | |
|---|---|---|---|---|---|---|
| time [hours] | | | | | | |
| Polymerisation temp. [°C] | 70.00 | 70.00 | 70.00 | 70.00 | 70.00 | 70.00 |
| Gross [g] | 569.07 | 568.52 | 572.42 | 565.48 | 567.42 | 574.41 |
| Tare [g] | 369.36 | 368.59 | 372.12 | 365.70 | 367.40 | 372.90 |
| Precipitate, moist [g] | 21.70 | 25.60 | 25.20 | 24.00 | 31.80 | 25.90 |
| Precipitate, dried [g] | 3.70 | 4.70 | 5.20 | 3.50 | 5.20 | 5.00 |
| Solids [%] | 0.36 | 0.34 | 0.40 | 0.47 | 0.31 | 0.65 |

Because the emulsifier action was inadequate, the use of these compounds led to two-phase mixtures which resulted in tacky and greasy dispersions.

Example 22: Polymerisation experiments with styrene

| | A | B | C | D | E | F |
|---|---|---|---|---|---|---|
| Deionised water, boiled [g] | 152.83 | 135.67 | 118.50 | 151.63 | 135.67 | 118.50 |
| 0.1 N sodium hydroxide solution [ml] | 2.33 | 4.65 | 6.98 | 3.53 | 7.07 | 10.60 |
| Styrene [g] | 30.00 | 30.00 | 30.00 | 30.00 | 30.00 | 30.00 |
| Example 11 (1%) [g] | 15.00 | 30.00 | 45.00 | | | |
| Example 12 (1%) [g] | | | | 15.00 | 30.00 | 45.00 |
| Polymarisation time [hours] | 15.00 | 15.00 | 15.00 | 15.00 | 15.00 | 15.00 |
| Polymerisation temp. [°C] | 70.00 | 70.00 | 70.00 | 70.00 | 70.00 | 70.00 |
| Gross [g] | 563.30 | 571.10 | 567.60 | 566.07 | 573.82 | 572.83 |
| Tare [g] | 364.11 | 371.08 | 367.14 | 365.93 | 371.29 | 368.20 |
| Precipitate, moist [g] | 20.00 | 22.60 | 22.00 | 26.00 | 27.90 | 33.30 |
| Precipitate, dried [g] | 4.50 | 6.50 | 7.60 | 1.50 | 2.30 | 3.30 |
| Solids [%] | 0.20 | 0.35 | 0.27 | 0.03 | 0.08 | 0.11 |

Because the emulsifier action as inadequate, the use of these compounds led to two-phase mixtures which resulted in tacky and greay dispersions.

Example 23: Polymerisation experiments with styrene

| | A | B | C |
|---|---|---|---|
| Deionised water, boiled [g] | 152.43 | 134.85 | 117.28 |
| 0.1 N sodium hydroxide solution [ml] | 2.73 | 5.47 | 8.21 |
| Styrene [g] | 30.00 | 30.00 | 30.00 |
| Example 13 (1%) [g] | 15.00 | 30.00 | 45.00 |
| Polymerisation time [hours] | 15.00 | 15.00 | 15.00 |
| Polymerisation temp. [°C] | 70.00 | 70.00 | 70.00 |
| Gross [g] | 568.00 | 571.26 | 570.76 |
| Tare [g] | 368.15 | 371.01 | 370.40 |
| Precipitate, moist [g] | 26.90 | 24.20 | 24.50 |
| Precipitate, dried [g] | 5.80 | 5.70 | 3.30 |
| Solids [%] | 0.13 | 0.33 | 0.11 |

Because the emulsifier action was inadequate, the use of these compounds led to two-phase mixtures which resulted in tacky and greasy dispersions.

Example 24: Polymerisation experiments with styrene

| | A | B | C | D | E | F |
|---|---|---|---|---|---|---|
| Deionised water, boiled [g] | 155 | 140 | 125 | 155 | 140 | 125 |
| Styrene [g] | 30 | 30 | 30 | 30 | 30 | 30 |
| Example 14 | 15 | 30 | 45 | | | |
| Example 15 | 15 | 30 | 45 | | | |
| Polymerisation time [h] | 15 | 15 | 15 | 15 | 15 | 15 |
| Temp. [°C] | 70 | 70 | 70 | 70 | 70 | 70 |
| Gross | 568.07 | 565.58 | 566.86 | 567.24 | 567.9 | 567.1 |
| Tare | 368.3 | 365.59 | 366.9 | 367.39 | 367.48 | 367.11 |
| Solids | 14.23 | 14.49 | 14.79 | 14.32 | 14.75 | 14.64 |
| Latex weight | 195.08 | 193.43 | 194.28 | 195.48 | 196.28 | 195.47 |
| Precipitate, moist | 1.04 | 1.09 | 0.92 | 0.78 | 0.62 | 0.9 |

-continued

| | | | | | | |
|---|---|---|---|---|---|---|
| Precipitate dry | 0.8 | 0.58 | 0.36 | 0.51 | 0.37 | 0.53 |

These examples show that a minimum number of C atoms is necessay to achieve an adequate action.

Example 25: Comparison Experiments

| | A | B | C | D | E | F | G | H | I |
|---|---|---|---|---|---|---|---|---|---|
| Deionised water [g] | 159.1 | 148.3 | 105.1 | 163.6 | 152.80 | 109.6 | 163.6 | 152.8 | 109.6 |
| Styrene [g] | 100.0 | 100.0 | 100.0 | 42.7 | 42.70 | 42.7 | 42.7 | 42.7 | 42 |
| n-Butyl acrylate [g] | 57.3 | 57.3 | 57.3 | 57.3 | 57.3 | 57.3 | 57.3 | 57.3 | 57 |
| Alkali metal alkanemonosulphonate having about 15 C atoms | 36.0 | 48.0 | 96.0 | 28.5 | 38.00 | 76.0 | | | |
| Alkali metal alkanedisulphonate having about 15 C atoms | | | | | | | 28.5 | 38.0 | 76.0 |
| Azodiisobutyric acid amidine, 10% [g] | 5.0 | 5.0 | 5.0 | 7.5 | 10.00 | 10.0 | 20.0 | 20.0 | 7 |
| Temp. [°C.] | 60.0 | 60.0 | 60.0 | 60.0 | 60.00 | 60.0 | 60.0 | 60.0 | 60.0 |
| Time [hours] | 7.0 | 7.0 | 7.0 | 7.0 | 7.00 | 7.0 | 7.0 | 7.0 | 7 |
| Solids content [%] | 31.9 | 338 | 30.8 | 33.8 | 34.80 | 34.6 | 345. | 31.2 | 31.4 |
| Electrical conductivity [mS] | 2.5 | 2.9 | 4.6 | 3.5 | 4.50 | 4.8 | 6.8 | 10.8 | 7 |
| Latex particle diameter [nm] | 108.0 | 107.0 | 95.0 | 94.0 | 90.00 | 153.0 | 79.0 | 150.0 | 220.0 |
| Foam regression time [sec] | >300.0 | >300.0 | >300.0 | >300.0 | >300.0 | >300.0 | >300.0 | >300.0 | >300.0 |

The electrical conductivity, which can be used as measure of chemical pollution of the wastewater, is smaller in the examples according to the invention than in the comparison by a factor of about 10, which clearly demonstrates the advantages of the new initiators.

Example 26: Comparison Example

| | A | B | C | D | E |
|---|---|---|---|---|---|
| Deionised water, boiled | 204.59 | 201.31 | 194.75 | 181.64 | 168.52 |
| Styrene [g] | 57 | 57 | 57 | 57 | 57 |
| Methacrylic acid [g] | 0.285 | 0.571 | 1.141 | 2.282 | 3.423 |
| Potassium hydroxide solution, 1 N [g] | 3.46 | 6.93 | 13.86 | 27.71 | 41.57 |
| 1% strength potassium persulphate solution [g] | 11.4 | 11.4 | 11.4 | 11.4 | 11.4 |
| 1% strength sodium carbonate solution [g] | 8.94 | 8.94 | 8.94 | 8.94 | 8.94 |
| Temp. [°C.] | 70 | 70 | 70 | 70 | 70 |
| Time [h] | 15 | 15 | 15 | 15 | 15 |
| Solids content [%] | 4.08 | 15.62 | 18.27 | 18.28 | 17.98 |
| Electrical conductivity | 1.98 | 3.00 | 4.77 | 8.67 | 12.47 |
| Latex particle diameter [nm] | >1000 | 790 | 672 | 483 | 396 |

Example 27: Comparison Example

| | A | B | C | D | E |
|---|---|---|---|---|---|
| Deionised water, boiled | 203.95 | 200.02 | 192.20 | 176.53 | 160.87 |
| Styrene [g] | 57 | 57 | 57 | 57 | 57 |
| Arylic acid [g] | 0.285 | 0.571 | 1.141 | 2.282 | 3.423 |
| Potassium hydroxide solution, | 4.13 | 8.28 | 16.55 | 33.11 | 49.66 |

-continued

| 1 N [g] | | | | | |
|---|---|---|---|---|---|
| 1% strength potassium persulphate solution [g] | 11.4 | 11.4 | 11.4 | 11.4 | 11.4 |
| 1% strength sodium carbonate solution [g] | 8.94 | 8.94 | 8.94 | 8.94 | 8.94 |
| Temp. [°C] | 70 | 70 | 70 | 70 | 70 |
| Time [h] | 15 | 15 | 15 | 15 | 15 |
| Solids content [%] | 16.73 | 8.41 | 17.37 | 16.62 | 18.36 |
| Electrical conductivity [mS] | 2.16 | 3.50 | 5.70 | 10.25 | 14.20 |
| Latex particle diameter [nm] | 767 | >1000 | 734 | 446 | 437 |

The electrical conductivity, which can be used as a measure of the chemical pollution of the wastewater, is also higher in these two comparison examples than in the examples according to the invention by a factor of about 10, which clearly demonstrates the advantages of the new initiators.

What is claimed is:

1. A peroxide of the formula $$X_n-A-\overset{O}{\underset{\|}{C}}-O-O-R^1 \quad (I)$$

wherein
$R^1$ denotes alkyl or cycloalkyl having 4 to 20 carbon atoms, and aryl radicals having 6 to 20 carbon atoms,
X denotes the radicals —COOH and —SO$_3$H and alkali metal, alkaline earth metal or ammonium salts thereof,
n denotes an integer in the range from 1 to 6, and wherein the radical A is corresponding to the formula (II)

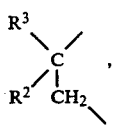

wherein
the radicals $R^2$ and $R^3$ represent H, $C_1$-$C_{40}$-alkyl, $C_3$-$C_{40}$-cycloalkyl, aryl, aralkyl or halogen, with the limitation that the sum of the carbon atoms in the two radicals is greater than 16.

2. A rocess for emulsion polymerization of olefinically unsaturated monomers which comprises adding a peroxide of the formula $$X_n-A-\overset{O}{\underset{\|}{C}}-O-O-R^1 \quad (I)$$

wherein
$R^1$ denotes alkyl or cycloalkyl having 4 to 20 carbon atoms, and aryl radicals having 6 to 20 carbon atoms,
X denotes the radicals —COOH and —SO$_3$H and alkali metal, alkaline earth metal or ammonium salts thereof,
n denotes an integer in the range from 1 to 6, and wherein the radical A is corresponding to the formula (II)

wherein
the radicals $R^2$ and $R^3$ represent H, $C_1$-$C_{40}$-alkyl, $C_3$-$C_{40}$-cycloalkyl, aryl, aralkyl or halogen, with the limitation that the sum of the carbon atoms in the two radicals is greater than 16, to at least one olefinically unsaturated monomer.

3. A process according to claim 2, wherein the peroxide concentration is 0.05 to 10% by weight, based on monomer of the peroxides.

4. A process according to claim 2 wherein the reaction temperature is between 35° and 90° C.

5. A process according to claim 2 wherein the olefinically unsaturated monomers are styrene, α-methylstyrene, butadiene, $C_1$-$C_8$-alkyl acrylates, $C_1$-$C_8$-alkyl methacrylates, acrylonitrile, methyacrylates, acrylonitrile, methoacrylonitrile, vinyl chloride, vinyl acetate, ethylene, chloroprene and mixtures thereof.

* * * * *

UNITED STATES PATENT AND TRADEMARK OFFICE
CERTIFICATE OF CORRECTION

PATENT NO. : 5,312,997
DATED : May 17, 1994
INVENTOR(S) : Bohnenpoll, et al.

It is certified that error appears in the above-indentified patent and that said Letters Patent is hereby corrected as shown below:

| | |
|---|---|
| Title Page & Col 1 line 1 | Title [54] Delete " PEREOXIDES " and substitute -- PEROXIDES -- |
| Col. 4, line 37 | Delete " nless " and substitute -- unless -- |
| Col. 7, line 12 | In EXAMPLE 17 under " Deionised " insert -- water -- |
| Col. 9 & 10 Example 19 | In Example 19 Wavelength = 600 nm [nm], Col A delete " 130.00 " and substitute -- 206.00--; Col B delete " 123.00 " and substitute -- 130.00 --; Col C delete " 475.00 " and substitute -- 123.00 --; Col D delete " 327.00 " and substitute -- 475.00 --; Col E delete " 170.00 " and substitute -- 327.00 --; Col F delete " 206.00 " and substitute -- 170.00 -- |
| Col. 9 & 10 Example 19 | In Example 19 Wavelength = 700 nm [nm] Col A delete " 127.00 " and substitute -- 201.00 --; Col B delete " 119.00 " and substitute -- 127.00 --; Col C delete 439.00 " and substitute -- 119.00 --; Col D delete " 313.00 " and substitute -- 439.00 --; Col E delete " 163.00 " and substitute 313.00 --; Col F delete " 201.00 " and substitute -- 163.00 -- |

UNITED STATES PATENT AND TRADEMARK OFFICE
CERTIFICATE OF CORRECTION

PATENT NO.   : 5,312,997
DATED        : May 17, 1994
INVENTOR(S)  : Bohnenpoll, et al.

It is certified that error appears in the above-indentified patent and that said Letters Patent is hereby corrected as shown below:

| | | |
|---|---|---|
| Col. 12, line 8 | Example 24 | Under " A, B, & C " delete " 15, 30, & 45 "; under " D, E, & F " insert -- 15, 30, & 45 -- |
| Col. 14, line 3 | Example 25 | Under " I " delete 42 and substitute -- 42.7 -- |
| Col. 14, line 4 | Example 25 | Under " I " delete " 57 " and substitute -- 57.3 -- |
| Col. 14, line 6 | Example 25 | Under " I " delete " 7 " and substitute -- 7.5 -- |
| Col. 14, line 10 | Example 25 | Under " B " delete " 338 " and substitute -- 33.8 -- |
| Col. 14, line 10 | Example 25 | Under " G " delete " 345 " and sub- -- 34.5 -- |
| Col. 14, line 11 | Example 25 | Under " I " delete " 7 " and substitute -- 7.8 -- |
| Col. 14, line 12 | Example 25 | Under and in between " E and F " delete " 153.0 "; under " F " delete " 79.0 " and insert -- 153.0 --; under " G " delete " 150.0 " and insert -- 79.0 --; under " H " delete " 220.0 " and insert -- 150.0--; under " I " insert -- 220.0 -- |

UNITED STATES PATENT AND TRADEMARK OFFICE
CERTIFICATE OF CORRECTION

PATENT NO. : 5,312,997
DATED : May 17, 1994
INVENTOR(S) : Bohnenpoll, et al..

It is certified that error appears in the above-indentified patent and that said Letters Patent is hereby corrected as shown below:

Col. 15, claim 2      Delete " rocess " and substitute
line 1                -- process --

Col. 16, claim 5      Delete " methyacrylates, acrylonitrile,
lines 4-5             methoacrylonitrile " and substitute
                      -- methacrylonitrile --

Signed and Sealed this

Fifth Day of August, 1997

*Attest:*

BRUCE LEHMAN

*Attesting Officer*     *Commissioner of Patents and Trademarks*